United States Patent
Bertin (10) Patent No.: US 10,036,598 B2
(45) Date of Patent: Jul. 31, 2018

(54) ALIPHATIC MATERIALS AND USES THEREOF IN HEATING AND COOLING APPLICATIONS

(71) Applicant: Elevance Renewable Sciences, Inc., Woodridge, IL (US)

(72) Inventor: Paul Bertin, Woodridge, IL (US)

(73) Assignee: Elevance Renewable Sciences, Inc., Woodridge, IL (US)

(*) Notice: Subject to any disclaimer, the term of this patent is extended or adjusted under 35 U.S.C. 154(b) by 0 days.

(21) Appl. No.: 15/099,599

(22) Filed: Apr. 15, 2016

(65) Prior Publication Data
US 2016/0305716 A1    Oct. 20, 2016

Related U.S. Application Data (60) Provisional application No. 62/148,263, filed on Apr. 16, 2015, provisional application No. 62/232,235, filed on Sep. 24, 2015.

(51) Int. Cl.

| | |
|---|---|
| *C07C 59/147* | (2006.01) |
| *F28D 20/02* | (2006.01) |
| *C07C 31/20* | (2006.01) |
| *C07C 55/02* | (2006.01) |
| *C07C 69/67* | (2006.01) |
| *C09K 5/06* | (2006.01) |
| *F28D 21/00* | (2006.01) |

(52) U.S. Cl.
CPC ............. *F28D 20/02* (2013.01); *C07C 31/20* (2013.01); *C07C 55/02* (2013.01); *C07C 69/67* (2013.01); *C09K 5/063* (2013.01); *F28D 2021/0061* (2013.01); *Y02E 60/145* (2013.01)

(58) Field of Classification Search
CPC ................. F28D 20/02; C07C 31/20
USPC .......................................... 554/121
See application file for complete search history.

(56) References Cited

U.S. PATENT DOCUMENTS

| | | | |
|---|---|---|---|
| 5,755,987 A * | 5/1998 | Goldstein | C09K 5/063 126/619 |
| 2009/0199994 A1 | 8/2009 | Amano | |
| 2014/0113112 A1 | 4/2014 | Koopmans et al. | |

FOREIGN PATENT DOCUMENTS

WO    WO 2015164654 A1 *   10/2015   ........... C09D 11/102

OTHER PUBLICATIONS

Aydin, "Diesters of high-chain dicarboxylic acids with 1-tetradecanol as novel organic phase change materials for thermal energy storage", Solar Energy Materials & Solar Cells (2012), vol. 104, pp. 102-108.*

Ohlman et al., J. Am. Chem. Soc., vol. 134, pp. 13716-13729 (2012).

(Continued)

*Primary Examiner* — Deborah D Carr
(74) *Attorney, Agent, or Firm* — Kilpatrick Townsend & Stockton LLP (57) ABSTRACT

Aliphatic materials and their use in passive heating and cooling applications are generally disclosed. In some embodiments, dibasic acids and esters (diesters) thereof and their use in passive heating and cooling applications are disclosed. In some embodiments, $C_{18}$ dibasic acids and esters thereof are disclosed, including their use in passive heating and cooling applications. In some embodiments, various olefins, including alkenes and olefinic acids and esters, are disclosed, including their use in passive heating and cooling applications.

12 Claims, 1 Drawing Sheet

(56) References Cited

OTHER PUBLICATIONS

Jimenez-Rodriguez et al., Inorg. Chem. Commun., vol. 8, pp. 878-881 (2005).
Int'l Search Report & Written Opinion of the Int'l Searching Authority, PCT App. No. PCT/2016/027643, dated Jul. 21, 2016.

* cited by examiner

ALIPHATIC MATERIALS AND USES THEREOF IN HEATING AND COOLING APPLICATIONS

CROSS-REFERENCE TO RELATED APPLICATIONS

The present application claims the benefit of priority of U.S. Provisional Application No. 62/148,263, filed Apr. 16, 2015; and 62/232,235, filed Sep. 24, 2015. Both of the foregoing applications are hereby incorporated by reference as though set forth in their entirety herein.

TECHNICAL FIELD

Aliphatic materials and their use in passive heating and cooling applications are generally disclosed. In some embodiments, dibasic acids and esters (diesters) thereof and their use in passive heating and cooling applications are disclosed. In some embodiments, $C_{18}$ dibasic acids and esters thereof are disclosed, including their use in passive heating and cooling applications. In some embodiments, various olefins, including alkenes, olefinic acids and esters, and diols, are disclosed, including their use in passive heating and cooling applications.

BACKGROUND

Phase-change materials (PCMs) are materials that are capable of storing or releasing energy in a latent manner during a reversible physical change of state. For example, such materials can store thermal energy if, in their liquid state, they are exposed to temperatures below their melting point, thereby inducing them to solidify and release an amount of energy corresponding to her heat of fusion. They can store thermal energy when this process is carried out in reverse. Such materials are useful because they can release and store much more thermal energy that typical insulating materials of comparable volume.

PCMs are all the more advantageous when the amount of heat exchanged during these phase changes is large. In the case of a solid/liquid transition, this is expressed by their heat of fusion or the heat of crystallization. The melting temperatures and crystallization temperatures of the PCMs furthermore determine the possible applications of the material. Typical uses include cooling food products or of pharmaceutical products that are sensitive to heat, cooling textile materials, cooling engines, cooling electronic components and circuits, or cooling waste combustion plants. On the industrial scale, PCMs also form a means for recovering heat that is released or that is available contained in containers or equipment (such as chemical reactors, generators of electrical or mechanical energy) or in process streams or fluids (for example cooling/heating circuits, effluents, etc.), especially during certain exothermic chemical reactions. The heat released may then be reused to provide energy to other reactions, which makes it possible to reduce the industrial consumption of fossil fuel-derived energy or electrical energy. The use of PCMs in air conditioning cycles (heating/cooling) is also an example of an application where it is possible to efficiently store thermal energy to then release it at the desired time and in the desired amount.

The most common PCM material is water. During its solid/liquid transition (and therefore implicitly liquid/solid transition), it makes it possible to absorb or release large amounts of heat. It is in this way that tanks or pools of water at temperatures near 0° C., which is free (in the form of an ice/liquid water mixture) or is encapsulated, for example in balls made of plastic or other materials, constitute a simple example of a PCM system capable of storing (during the melting of the ice) and of releasing (during the crystallization of the liquid water) large amounts of energy per unit mass of water. But water, although readily available and non-toxic, cannot solve all the possible problems due to its restricted usage range (around 0° C.) and problems linked to the high volume expansion of the ice during its formation.

Other common PCMs include paraffins and fatty acids, such as dodecanoic acid, hydrated salts such as manganese (II) nitrate dihydrate, certain eutectic mixtures, such as mixtures of capric acid and of lauric acid. These compounds generally have quite low melting temperatures, ranging from 15 to 48° C. Even so, these PCMs have many drawbacks impeding their industrial development. In particular, organic PCMs may be inflammable, have a low thermal conductivity in the solid state, require high heat transfers during the freezing cycle, and have a low volumetric latent heat. Furthermore, paraffins may pose problems of supply, cost and generation of $CO_2$ due to their petroleum origin. Inorganic PCMs generate, for their part, significant supercooling phenomena. Moreover, their phase transition temperatures are not constant due, in particular, to their hygroscopicity. Finally, they are capable of resulting in a corrosion of the metals with which they are in contact.

Therefore, there is a continuing need to develop additional PCMs that have a high heat of fusion, have melting points that occur at practical temperatures for various applications, and overcome other of the aforementioned problems.

SUMMARY

In a first aspect, the disclosure provides compounds of formula (I):

(I)

wherein: $X^1$ is $C_{11-24}$ alkylene or $C_{11-24}$ alkenylene, each of which is optionally substituted one or more times by substituents selected independently from $R^x$; $R^1$ is $C_{1-12}$ alkyl, $C_{2-12}$ alkenyl, $C_{1-12}$ oxyalkyl, $C_{3-12}$ cycloalkyl, or $C_{2-12}$ heterocyclyl, each of which is optionally substituted one or more times by substituents selected independently from $R^x$, or $R^1$ is a hydrogen atom; $R^2$ is a $C_{1-12}$ alkyl, $C_{2-12}$ alkenyl, $C_{1-12}$ oxyalkyl, $C_{3-12}$ cycloalkyl, or $C_{2-12}$ heterocyclyl, each of which is optionally substituted one or more times by substituents selected independently from $R^x$, or $R^2$ is a hydrogen atom; and $R^x$ is a halogen atom, —OH, —$NH_2$, $C_{1-6}$ alkyl, $C_{1-6}$ heteroalkyl, or $C_{2-6}$ alkenyl.

In a second aspect, the disclosure provides passive heating and cooling compositions, including one or more compounds of the first aspect.

In a third aspect, the disclosure provides passive heating and cooling compositions that comprise one or more compounds selected from the group consisting of: 9-octadecene, octadecanes, pentadecanes, tridecanes, methyl tridecanoate, and methyl pentadecanoate.

In a fourth aspect, the disclosure provides structures, apparatuses, or materials comprising one or more compounds of the first aspect or one or more compositions of the second or third aspects. In some embodiments, the structures, apparatuses, or materials include the following: polymer composites (such as a polymer composite comprising metal wires, metal particles, glass fibers, glass particles, and the like); wax composites (such as a wax composite comprising metal wires, metal particles, glass fibers, glass particles, and the like); insulation materials surrounding parts of a heating apparatus (such as furnaces, ovens, boilers, air ducts, pipes, and the like); insulated storage units; food or drink containers; building materials; medical equipment (such as containers for blood, other biological fluids, and biological tissue, operating tables, and the like); medical packaging, such as hot-cold therapies; textile fibers; clothing articles, jackets, coats, boots, shoes, hats, gloves, scarves, and the like; waste heat recovery apparatuses; water heating and cooling apparatuses; heat pump systems; passive storage structures in bioclimatic buildings; apparatuses for reducing exothermic temperature peaks in chemical reactors or reaction vessels; solar power plants; space suits; spacecraft; vehicle compartment insulation systems; electronic device insulation systems; battery cell insulation or safety systems; computer cooling systems; turbine inlet cooling systems; thermal energy storage systems; and telecommunications shelters.

In a fifth aspect, the disclosure provides methods of storing or releasing thermal energy, the methods comprising: using a compound of the first aspect or a composition of the second or third aspects, or a structure, apparatus, or material of the fourth aspect.

Further aspects and embodiments are provided in the foregoing drawings, detailed description and claims.

BRIEF DESCRIPTION OF THE DRAWINGS

The following drawings are provided for purposes of illustrating various embodiments of the compositions and methods disclosed herein. The drawings are provided for illustrative purposes only, and are not intended to describe any preferred compositions or preferred methods, or to serve as a source of any limitations on the scope of the claimed inventions.

DETAILED DESCRIPTION

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, "polymer" refers to a substance having a chemical structure that includes the multiple repetition of constitutional units formed from substances of comparatively low relative molecular mass relative to the molecular mass of the polymer. The term "polymer" includes soluble and/or fusible molecules having chains of repeat units, and also includes insoluble and infusible networks. As used herein, the term "polymer" can include oligomeric materials, which have only a few (e.g., 5-100) constitutional units As used herein, "natural oil," "natural feedstock," or "natural oil feedstock" refer to oils derived from plants or animal sources. These terms include natural oil derivatives, unless otherwise indicated. The terms also include modified plant or animal sources (e.g., genetically modified plant or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

As used herein, "natural oil derivatives" refers to the compounds or mixtures of compounds derived from a natural oil using any one or combination of methods known in the art. Such methods include but are not limited to saponification, fat splitting, transesterification, esterification, hydrogenation (partial, selective, or full), isomerization, oxidation, and reduction. Representative non-limiting examples of natural oil derivatives include gums, phospholipids, soapstock, acidulated soapstock, distillate or distillate sludge, fatty acids and fatty acid alkyl ester (e.g. non-limiting examples such as 2-ethylhexyl ester), hydroxy substituted variations thereof of the natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized soybean oil (i.e., RBD soybean oil). Soybean oil typically comprises about 95% weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9, 12-octadecadienoic acid), and linolenic acid (9,12,15-octadecatrienoic acid).

As used herein, "metathesis catalyst" includes any catalyst or catalyst system that catalyzes an olefin metathesis reaction.

As used herein, "metathesize" or "metathesizing" refer to the reacting of a feedstock in the presence of a metathesis catalyst to form a "metathesized product" comprising new olefinic compounds, i.e., "metathesized" compounds. Metathesizing is not limited to any particular type of olefin metathesis, and may refer to cross-metathesis (i.e., cometathesis), self-metathesis, ring-opening metathesis, ring-opening metathesis polymerizations ("ROMP"), ring-closing metathesis ("RCM"), and acyclic diene metathesis ("ADMET"). In some embodiments, metathesizing refers to reacting two triglycerides present in a natural feedstock (self-metathesis) in the presence of a metathesis catalyst, wherein each triglyceride has an unsaturated carbon-carbon double bond, thereby forming a new mixture of olefins and esters which may include a triglyceride dimer. Such triglyceride dimers may have more than one olefinic bond, thus higher oligomers also may form. Additionally, in some other embodiments, metathesizing may refer to reacting an olefin, such as ethylene, and a triglyceride in a natural feedstock having at least one unsaturated carbon-carbon double bond, thereby forming new olefinic molecules as well as new ester molecules (cross-metathesis).

As used herein, "olefin" or "olefins" refer to compounds having at least one unsaturated carbon-carbon double bond. In certain embodiments, the term "olefins" refers to a group of unsaturated carbon-carbon double bond compounds with different carbon lengths. Unless noted otherwise, the terms "olefin" or "olefins" encompasses "polyunsaturated olefins" or "poly-olefins," which have more than one carbon-carbon double bond. As used herein, the term "monounsaturated olefins" or "mono-olefins" refers to compounds having only one carbon-carbon double bond. A compound having a terminal carbon-carbon double bond can be referred to as a "terminal olefin" or an "alpha-olefin," while an olefin having a non-terminal carbon-carbon double bond can be referred to as an "internal olefin." In some embodiments, the alpha-olefin is a terminal alkene, which is an alkene (as defined below) having a terminal carbon-carbon double bond. Additional carbon-carbon double bonds can be present.

The number of carbon atoms in any group or compound can be represented by the terms: "$C_z$", which refers to a group of compound having z carbon atoms; and "$C_{x-y}$", which refers to a group or compound containing from x to y, inclusive, carbon atoms. For example, "$C_{1-6}$ alkyl" represents an alkyl chain having from 1 to 6 carbon atoms and, for example, includes, but is not limited to, methyl, ethyl, n-propyl, isopropyl, isobutyl, n-butyl, sec-butyl, tert-butyl, isopentyl, n-pentyl, neopentyl, and n-hexyl. As a further example, a "$C_{4-10}$ alkene" refers to an alkene molecule having from 4 to 10 carbon atoms, and, for example, includes, but is not limited to, 1-butene, 2-butene, isobutene, 1-pentene, 1-hexene, 3-hexene, 1-heptene, 3-heptene, 1-octene, 4-octene, 1-nonene, 4-nonene, and 1-decene.

As used herein, the term "low-molecular-weight olefin" may refer to any one or combination of unsaturated straight, branched, or cyclic hydrocarbons in the $C_{2-14}$ range. Low-molecular-weight olefins include alpha-olefins, wherein the unsaturated carbon-carbon bond is present at one end of the compound. Low-molecular-weight olefins may also include dienes or trienes. Low-molecular-weight olefins may also include internal olefins or "low-molecular-weight internal olefins." In certain embodiments, the low-molecular-weight internal olefin is in the $C_{4-14}$ range. Examples of low-molecular-weight olefins in the $C_{2-6}$ range include, but are not limited to: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. Non-limiting examples of low-molecular-weight olefins in the $C_{7-9}$ range include 1,4-heptadiene, 1-heptene, 3,6-nonadiene, 3-nonene, 1,4,7-octatriene. Other possible low-molecular-weight olefins include styrene and vinyl cyclohexane. In certain embodiments, it is preferable to use a mixture of olefins, the mixture comprising linear and branched low-molecular-weight olefins in the $C_{4-10}$ range. Olefins in the $C_{4-10}$ range can also be referred to as "short-chain olefins," which can be either branched or unbranched. In one embodiments, it may be preferable to use a mixture of linear and branched $C_4$ olefins (i.e., combinations of: 1-butene, 2-butene, and/or isobutene). In other embodiments, a higher range of $C_{11-14}$ may be used.

In some instances, the olefin can be an "alkene," which refers to a straight- or branched-chain non-aromatic hydrocarbon having 2 to 30 carbon atoms and one or more carbon-carbon double bonds, which may be optionally substituted, as herein further described, with multiple degrees of substitution being allowed. A "monounsaturated alkene" refers to an alkene having one carbon-carbon double bond, while a "polyunsaturated alkene" refers to an alkene having two or more carbon-carbon double bonds. A "lower alkene," as used herein, refers to an alkene having from 2 to 10 carbon atoms.

As used herein, "ester" or "esters" refer to compounds having the general formula: R—COO—R', wherein R and R' denote any organic group (such as alkyl, aryl, or silyl groups) including those bearing heteroatom-containing substituent groups. In certain embodiments, R and R' denote alkyl, alkenyl, aryl, or alcohol groups. In certain embodiments, the term "esters" may refer to a group of compounds with the general formula described above, wherein the compounds have different carbon lengths. In certain embodiments, the esters may be esters of glycerol, which is a trihydric alcohol. The term "glyceride" can refer to esters where one, two, or three of the —OH groups of the glycerol have been esterified.

It is noted that an olefin may also comprise an ester, and an ester may also comprise an olefin, if the R or R' group in the general formula R—COO—R' contains an unsaturated carbon-carbon double bond. Such compounds can be referred to as "unsaturated esters" or "olefin ester" or "olefinic ester compounds." Further, a "terminal olefinic ester compound" may refer to an ester compound where R has an olefin positioned at the end of the chain. An "internal olefin ester" may refer to an ester compound where R has an olefin positioned at an internal location on the chain. Additionally, the term "terminal olefin" may refer to an ester or an acid thereof where R' denotes hydrogen or any organic compound (such as an alkyl, aryl, or silyl group) and R has an olefin positioned at the end of the chain, and the term "internal olefin" may refer to an ester or an acid thereof where R' denotes hydrogen or any organic compound (such as an alkyl, aryl, or silyl group) and R has an olefin positioned at an internal location on the chain.

As used herein, "acid," "acids," "carboxylic acid," or "carboxylic acids" refer to compounds having the general formula: R—COOH, wherein R denotes any organic moiety (such as alkyl, aryl, or silyl groups), including those bearing heteroatom-containing substituent groups. In certain embodiments, R denotes alkyl, alkenyl, aryl, or alcohol groups. In certain embodiments, the term "acids" or "carboxylic acids" may refer to a group of compounds with the general formula described above, wherein the compounds have different carbon lengths.

As used herein, "alcohol" or "alcohols" refer to compounds having the general formula: R—OH, wherein R denotes any organic moiety (such as alkyl, aryl, or silyl groups), including those bearing heteroatom-containing substituent groups. In certain embodiments, R denotes alkyl, alkenyl, aryl, or alcohol groups. In certain embodiments, the term "alcohol" or "alcohols" may refer to a group of compounds with the general formula described above, wherein the compounds have different carbon lengths. As used herein, the term "alkanol" refers to alcohols where R is an alkyl group.

As used herein, "alkyl" refers to a straight or branched chain saturated hydrocarbon having 1 to 30 carbon atoms, which may be optionally substituted, as herein further described, with multiple degrees of substitution being allowed. Examples of "alkyl," as used herein, include, but are not limited to, methyl, ethyl, n-propyl, isopropyl, isobutyl, n-butyl, sec-butyl, tert-butyl, isopentyl, n-pentyl, neopentyl, n-hexyl, and 2-ethylhexyl. The number of carbon atoms in an alkyl group is represented by the phrase "$C_{x-y}$ alkyl," which refers to an alkyl group, as herein defined, containing from x to y, inclusive, carbon atoms. Thus, "$C_{1-6}$ alkyl" represents an alkyl chain having from 1 to 6 carbon atoms and, for example, includes, but is not limited to, methyl, ethyl, n-propyl, isopropyl, isobutyl, n-butyl, sec-butyl, tert-butyl, isopentyl, n-pentyl, neopentyl, and n-hexyl. In some instances, the "alkyl" group can be divalent, in which case the group can alternatively be referred to as an "alkylene" group. Also, in some instances, one or more of the carbon atoms in the alkyl or alkylene group can be replaced by a heteroatom (e.g., selected from nitrogen, oxygen, or sulfur, including N-oxides, sulfur oxides, and sulfur dioxides, where feasible), and is referred to as a "heteroalkyl" or "heteroalkylene" group, respectively. Non-limiting examples include "oxyalkyl" or "oxyalkylene" groups, which are groups of the following formulas: -[-(alkylene)-O]$_x$-alkyl, or -[-(alkylene)-O-]$_x$-alkylene-, respectively, where x is 1 or more, such as 1, 2, 3, 4, 5, 6, 7, or 8.

As used herein, "alkenyl" refers to a straight or branched chain non-aromatic hydrocarbon having 2 to 30 carbon atoms and having one or more carbon-carbon double bonds, which may be optionally substituted, as herein further described, with multiple degrees of substitution being allowed. Examples of "alkenyl," as used herein, include, but are not limited to, ethenyl, 2-propenyl, 2-butenyl, and 3-butenyl. The number of carbon atoms in an alkenyl group is represented by the phrase "$C_{x-y}$ alkenyl," which refers to an alkenyl group, as herein defined, containing from x to y, inclusive, carbon atoms. Thus, "$C_{2-6}$ alkenyl" represents an alkenyl chain having from 2 to 6 carbon atoms and, for example, includes, but is not limited to, ethenyl, 2-propenyl, 2-butenyl, and 3-butenyl. In some instances, the "alkenyl" group can be divalent, in which case the group can alternatively be referred to as an "alkenylene" group.

As used herein, "cycloalkyl" refers to an aliphatic saturated or unsaturated hydrocarbon ring system having 1 to 20 carbon atoms, which may be optionally substituted, as herein further described, with multiple degrees of substitution being allowed. In some embodiments, the term refers only to saturated hydrocarbon ring systems, substituted as indicated above. Examples of "cycloalkyl," as used herein, include, but are not limited to, cyclopropyl, cyclobutyl, cyclopentyl, cyclohexyl, cyclohexenyl, cycloheptyl, cyclooctyl, adamantyl, and the like. The number of carbon atoms in a cycloalkyl group is represented by the phrase "$C_{x-y}$ cycloalkyl," which refers to a cycloalkyl group, as herein defined, containing from x to y, inclusive, carbon atoms. Thus, "$C_{3-10}$ cycloalkyl" represents a cycloalkyl having from 3 to 10 carbon atoms and, for example, includes, but is not limited to, cyclopropyl, cyclobutyl, cyclopentyl, cyclohexyl, cyclohexenyl, cycloheptyl, cyclooctyl, and adamantyl. In some instances, the "cycloalkyl" group can be divalent, in which case the group can alternatively be referred to as a "cycloalkylene" group. Cycloalkyl and cycloalkylene groups can also be referred to herein as "carbocyclic rings." Also, in some instances, one or more of the carbon atoms in the cycloalkyl or cycloalkylene group can be replaced by a heteroatom (e.g., selected independently from nitrogen, oxygen, silicon, or sulfur, including N-oxides, sulfur oxides, and sulfur dioxides, where feasible), and is referred to as a "heterocyclyl" or "heterocyclylene" group, respectively. The term "heterocyclic ring" can also be used interchangeable with either of these terms. In some embodiments, the cycloalkyl and heterocyclyl groups are fully saturated. In some other embodiments, the cycloalkyl and heterocyclyl groups can contain one or more carbon-carbon double bonds.

As used herein, the term "branched," for example, in reference to an alkyl or alkenyl group, refers to the presence of one or more carbon atoms having three or four connections to other carbon atoms. By contrast, the term "unbranched" refers to groups not having any carbon atoms with three or four connections to other carbon atoms. For example, groups such as isopropyl, isobutyl, sec-butyl, and tert-butyl are branched, and groups such as n-propyl and n-butyl are unbranched. In some instances, it may be desirable to refer to a position for the branching, such as in the alcoholic portion of an ester. In such instances, the carbon atom immediately adjacent to the oxygen atom on the alcoholic side of the ester is the 1-position, the next in the 2-position, and so on. Thus, the alkyl group of sec-butyl alcohol or isopropyl alcohol is said to be branched at the 1-position, and the alkyl group of isobutyl alcohol is said to be branched at the 2-position and not branched at the 1-position, and so forth. The same principles apply to alkenyl groups, as the double bond does not count as 2 connections. Thus, groups like 9-octedenenyl are said to be unbranched, while a group like 1-methyl-9-octadenenyl is said to be branched, i.e., at the 1-position.

As used herein, "halogen" or "halo" refers to a fluorine, chlorine, bromine, and/or iodine atom. In some embodiments, the terms refer to fluorine or chlorine.

As used herein, "substituted" refers to substitution of one or more hydrogen atoms of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient. As used herein, the phrases "substituted with one or more . . . " or "substituted one or more times . . . " refer to a number of substituents that equals from one to the maximum number of substituents possible based on the number of available bonding sites, provided that the above conditions of stability and chemical feasibility are met.

As used herein, "mix" or "mixed" or "mixture" refers broadly to any combining of two or more compositions. The two or more compositions need not have the same physical state; thus, solids can be "mixed" with liquids, e.g., to form a slurry, suspension, or solution. Further, these terms do not require any degree of homogeneity or uniformity of composition. This, such "mixtures" can be homogeneous or heterogeneous, or can be uniform or non-uniform. Further, the terms do not require the use of any particular equipment to carry out the mixing, such as an industrial mixer.

As used herein, "optionally" means that the subsequently described event(s) may or may not occur. In some embodiments, the optional event does not occur. In some other embodiments, the optional event does occur one or more times.

As used herein, "comprise" or "comprises" or "comprising" or "comprised of" refer to groups that are open, meaning that the group can include additional members in addition to those expressly recited. For example, the phrase, "comprises A" means that A must be present, but that other members can be present too. The terms "include," "have," and "composed of" and their grammatical variants have the same meaning. In contrast, "consist of" or "consists of" or "consisting of" refer to groups that are closed. For example, the phrase "consists of A" means that A and only A is present.

As used herein, "or" is to be given its broadest reasonable interpretation, and is not to be limited to an either/or construction. Thus, the phrase "comprising A or B" means that A can be present and not B, or that B is present and not A, or that A and B are both present. Further, if A, for example, defines a class that can have multiple members, e.g., $A_1$ and $A_2$, then one or more members of the class can be present concurrently.

As used herein, the various functional groups represented will be understood to have a point of attachment at the functional group having the hyphen or dash (-) or an asterisk (*). In other words, in the case of —CH$_2$CH$_2$CH$_3$, it will be understood that the point of attachment is the CH$_2$ group at the far left. If a group is recited without an asterisk or a dash, then the attachment point is indicated by the plain and ordinary meaning of the recited group.

As used herein, multi-atom bivalent species are to be read from left to right. For example, if the specification or claims recite A-D-E and D is defined as —OC(O)—, the resulting group with D replaced is: A-OC(O)-E and not A-C(O)O-E.

Other terms are defined in other portions of this description, even though not included in this subsection.

Compounds for Passive Heating and Cooling

In certain aspects, the disclosure provides compounds that are dibasic acids or esters thereof (e.g., diesters formed from various aliphatic alcohols). In some embodiments, the dibasic acid is a $C_{14-24}$ aliphatic dibasic acid, such as a $C_{18}$ aliphatic dibasic acid (e.g., 1,18 octadecanedioic acid). In some embodiments, the phase-change compounds are aliphatic diesters of any of the aforementioned dibasic acids, such as dimethyl esters.

Figure 1:
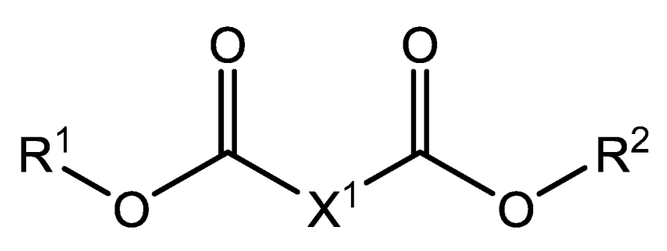
FIG. 1 shows a non-limiting example of a compound made according to certain embodiments disclosed herein, wherein: $X^1$ is $C_{11-24}$ alkylene or $C_{11-24}$ alkenylene, each of which is optionally substituted; $R^1$ is $C_{1-12}$ alkyl, $C_{2-12}$ alkenyl, $C_{1-12}$ oxyalkyl, $C_{3-12}$ cycloalkyl, or $C_{2-12}$ heterocyclyl, each of which is optionally substituted, or $R^1$ is a hydrogen atom; $R^2$ is a $C_{1-12}$ alkyl, $C_{2-12}$ alkenyl, $C_{1-12}$ oxyalkyl, $C_{3-12}$ cycloalkyl, or $C_{2-12}$ heterocyclyl, each of which is optionally substituted, or $R^2$ is a hydrogen atom.

In a some embodiments, the disclosure provides compounds of formula (I)

wherein: $X^1$ is $C_{11-24}$ alkylene or $C_{11-24}$ alkenylene, each of which is optionally substituted one or more times by substituents selected independently from $R^x$; $R^1$ is $C_{1-12}$ alkyl, $C_{2-12}$ alkenyl, $C_{1-12}$ oxyalkyl, $C_{3-12}$ cycloalkyl, or $C_{2-12}$ heterocyclyl, each of which is optionally substituted one or more times by substituents selected independently from $R^x$, or $R^1$ is a hydrogen atom; $R^2$ is a $C_{1-12}$ alkyl, $C_{2-12}$ alkenyl, $C_{1-12}$ oxyalkyl, $C_{3-12}$ cycloalkyl, or $C_{2-12}$ heterocyclyl, each of which is optionally substituted one or more times by substituents selected independently from $R^x$, or $R^2$ is a hydrogen atom; and $R^x$ is a halogen atom, —OH, —NH$_2$, $C_{1-6}$ alkyl, $C_{1-6}$ heteroalkyl, or $C_{2-6}$ alkenyl.

In some embodiments of any of the aforementioned embodiments, $X^1$ is $C_{11-24}$ alkylene, which is optionally substituted one or more times by substituents selected independently from $R^x$. In some further such embodiments, $X^1$ is $C_{11-24}$ alkylene, which is optionally substituted one or more times by substituents selected independently from the group consisting of —OH and $C_{1-6}$ oxyalkyl. In some further such embodiments, $X^1$ is $C_{12-20}$ alkylene, which is optionally substituted one or more times by substituents selected independently from the group consisting of —OH and $C_{1-6}$ oxyalkyl. In some further such embodiments, $X^1$ is —(CH$_2$)$_{12}$—, —(CH$_2$)$_{14}$—, —(CH$_2$)$_{16}$—, —(CH$_2$)$_{18}$—, —(CH$_2$)$_{20}$—, or —(CH$_2$)$_{22}$—. In some further embodiments, $X^1$ is —(CH$_2$)$_{16}$—.

In some embodiments of any of the aforementioned embodiments, $X^1$ is $C_{11-24}$ alkenylene, which is optionally substituted one or more times by substituents selected independently from $R^x$. In some further such embodiments, $X^1$ is $C_{11-24}$ alkenylene, which is optionally substituted one or more times by substituents selected independently from the group consisting of —OH and $C_{1-6}$ oxyalkyl. In some further such embodiments, $X^1$ is $C_{12-20}$ alkenylene, which is optionally substituted one or more times by substituents selected independently from the group consisting of —OH and $C_{1-6}$ oxyalkyl. In some further such embodiments, $X^1$ is —(CH$_2$)$_7$—CH═CH—(CH$_2$)$_7$—. In the aforementioned embodiments, the carbon-carbon double bond(s) can have a Z or E configuration, or some combination thereof. In some embodiments, however, the alkenylene group has one carbon-carbon double bond and has a Z configuration, such as —(CH$_2$)$_7$—CH═CH—(CH$_2$)$_7$— having a Z configuration. In some other embodiments, the alkenylene group has one carbon-carbon double bond and has an E configuration, such as —(CH$_2$)$_7$—CH═CH—(CH$_2$)$_7$— having a E configuration.

In some embodiments of any of the aforementioned embodiments, $R^1$ is a hydrogen atom.

In some embodiments of any of the aforementioned embodiments, $R^1$ is $C_{1-12}$ alkyl, which is optionally substituted one or more times by substituents selected independently from $R^x$. In some further such embodiments, $R^1$ is an unbranched $C_{1-12}$ alkyl, which is optionally substituted one or more times by substituents selected independently from the group consisting of —OH and $C_{1-6}$ oxyalkyl. In some further such embodiments, $R^1$ is methyl, ethyl, propyl, butyl, pentyl, hexyl, heptyl, or octyl. In some such embodiments, $R^1$ is methyl. In some such embodiments, $R^1$ is ethyl. In some such embodiments, $R^1$ propyl. In some other embodiments, $R^1$ is —$CH_2$—OH, —$CH_2$—$CH_2$—OH, —CH(—$CH_3$)—$CH_2$—OH, or —$CH_2$—CH(—OH)—$CH_3$. In some other embodiments, $R^1$ is a branched $C_{1-12}$ alkyl, which is optionally substituted one or more times by substituents selected independently from the group consisting of —OH and $C_{1-6}$ oxyalkyl. In some further such embodiments, $R^1$ is a branched $C_{1-12}$ alkyl that comprises branching at the α-position (i.e., at the carbon atom immediately adjacent to the alcoholic oxygen of the ester group), such as where $R^1$ is isopropyl, sec-butyl, or tert-butyl. In some embodiments, $R^1$ is a branched $C_{1-12}$ alkyl that comprises branching at the β-position (i.e., at the second carbon atom from the alcoholic oxygen of the ester group), such as where $R^1$ is isobutyl or 2-ethylhexyl. In some embodiments, $R^1$ is 2-ethylhexyl. In some embodiments, $R^1$ is a branched $C_{1-12}$ alkyl that comprises branching at the ψ-position (i.e., at the penultimate carbon atom from the alcoholic oxygen of the ester group), such as where $R^1$ is isobutyl, isoamyl, neopentyl, or 3,5,5-trimethylhexyl. In some embodiments, $R^1$ is isoamyl (3-methylbutyl). In some embodiments, $R^1$ is 3,5,5-trimethylhexyl.

In some embodiments of any of the aforementioned embodiments, $R^1$ is $C_{1-12}$ oxyalkyl, which is optionally substituted one or more times by substituents selected independently from the group consisting of —OH and $C_{1-6}$ oxyalkyl. In some embodiments, $R^1$ is selected from the group consisting of: —$CH_2$—$CH_2$—O—$R^3$, —$CH_2$—CH(O—$R^4$)—$CH_3$, —$CH_2$—$CH_2$—$CH_2$—O—$R^5$, —$CH_2$—$CH_2$—$CH_2$—$CH_2$—O—$R^6$, —$CH_2$—$CH_2$(—O—$CH_2$—$CH_2$)$_w$—OH, —$CH_2$—$CH_2$(—O—$CH_2$—$CH_2$)$_x$—O—$R^7$; —$CH_2$—CH(—$CH_3$)(—O—$CH_2$—CH(—$CH_3$))$_y$—OH, and —$CH_2$—CH(—$CH_3$)(—O—$CH_2$—CH(—$CH_3$))$_z$—O—$R^8$; wherein $R^3$, $R^4$, $R^5$, $R^6$, $R^7$, and $R^8$ are independently methyl or ethyl; and w, x, y, and z are independently an integer from 1 to 10. In some embodiments, w, x, y, and z are independently 1, 2, or 3. In some embodiments, w, x, y, and z are independently 4, 5, or 6. In some such embodiments, $R^1$ is —$CH_2$—$CH_2$—O—$CH_3$. In some such embodiments, $R^1$ is —$CH_2$—$CH_2$—O—$CH_2$—$CH_2$—O—$CH_3$. In some such embodiments, $R^1$ is —$CH_2$—$CH_2$(—O—$CH_2$—$CH_2$)$_{1-10}$—O—$CH_3$. In some such embodiments, $R^1$ is —$CH_2$—$CH_2$(—O—$CH_2$—$CH_2$)$_2$—O—$CH_3$. In some such embodiments, $R^1$ is —$CH_2$—$CH_2$(—O—$CH_2$—$CH_2$)$_3$—O—$CH_3$. In some such embodiments, $R^1$ is —$CH_2$—$CH_2$(—O—$CH_2$—$CH_2$)$_4$—O—$CH_3$. In some such embodiments, $R^1$ is —$CH_2$—$CH_2$(—O—$CH_2$—$CH_2$)$_5$—O—$CH_3$. In some such embodiments, $R^1$ is —$CH_2$—$CH_2$(—O—$CH_2$—$CH_2$)$_6$—O—$CH_3$. In some such embodiments, $R^1$ is —$CH_2$—$CH_2$(—O—$CH_2$—$CH_2$)$_7$—O—$CH_3$. In some such embodiments, $R^1$ is —$CH_2$—$CH_2$(—O—$CH_2$—$CH_2$)$_8$—O—$CH_3$.

In some embodiments of any of the aforementioned embodiments, $R^1$ is $C_{3-12}$ cycloalkyl, which is optionally substituted one or more times by substituents selected independently from $R^x$. In some such embodiments, $R^1$ is cyclopentyl. In some such embodiments, $R^1$ is cyclohexyl.

In some embodiments of any of the aforementioned embodiments, $R^2$ is a hydrogen atom.

In some embodiments of any of the aforementioned embodiments, $R^2$ is $C_{1-12}$ alkyl, which is optionally substituted one or more times by substituents selected independently from $R^x$. In some further such embodiments, $R^2$ is an unbranched $C_{1-12}$ alkyl, which is optionally substituted one or more times by substituents selected independently from the group consisting of —OH and $C_{1-6}$ oxyalkyl. In some further such embodiments, $R^2$ is methyl, ethyl, propyl, butyl, pentyl, hexyl, heptyl, or octyl. In some such embodiments, $R^2$ is methyl. In some such embodiments, $R^2$ is ethyl. In some such embodiments, $R^2$ propyl. In some other embodiments, $R^2$ is —$CH_2$—OH, —$CH_2$—$CH_2$—OH, —CH(—$CH_3$)—$CH_2$—OH, or —$CH_2$—CH(—OH)—$CH_3$. In some other embodiments, $R^2$ is a branched $C_{1-12}$ alkyl, which is optionally substituted one or more times by substituents selected independently from the group consisting of —OH and $C_{1-6}$ oxyalkyl. In some further such embodiments, $R^2$ is a branched $C_{1-12}$ alkyl that comprises branching at the α-position (i.e., at the carbon atom immediately adjacent to the alcoholic oxygen of the ester group), such as where $R^2$ is isopropyl, sec-butyl, or tert-butyl. In some embodiments, $R^2$ is a branched $C_{1-12}$ alkyl that comprises branching at the β-position (i.e., at the second carbon atom from the alcoholic oxygen of the ester group), such as where $R^2$ is isobutyl or 2-ethylhexyl. In some embodiments, $R^2$ is 2-ethylhexyl. In some embodiments, $R^2$ is a branched $C_{1-12}$ alkyl that comprises branching at the ψ-position (i.e., at the penultimate carbon atom from the alcoholic oxygen of the ester group), such as where $R^2$ is isobutyl, isoamyl, neopentyl, or 3,5,5-trimethylhexyl. In some embodiments, $R^2$ is isoamyl (3-methylbutyl). In some embodiments, $R^2$ is 3,5,5-trimethylhexyl.

In some embodiments of any of the aforementioned embodiments, $R^2$ is $C_{1-12}$ oxyalkyl, which is optionally substituted one or more times by substituents selected independently from the group consisting of —OH and $C_{1-6}$ oxyalkyl. In some embodiments, $R^2$ is selected from the group consisting of: —$CH_2$—$CH_2$—O—$R^{13}$, —$CH_2$—CH(O—$R^{14}$)—$CH_3$, —$CH_2$—$CH_2$—$CH_2$—O—$R^{15}$, —$CH_2$—$CH_2$—$CH_2$—$CH_2$—O—$R^{16}$, —$CH_2$—$CH_2$(—O—$CH_2$—$CH_2$)$_{w'}$—OH, —$CH_2$—$CH_2$(—O—$CH_2$—$CH_2$)$_{x'}$—O—$R^{17}$, —$CH_2$—CH(—$CH_3$)(—O—$CH_2$—CH(—$CH_3$))$_{y'}$—OH, and —$CH_2$—CH(—$CH_3$)(—O—$CH_2$—CH(—$CH_3$))$_{z'}$—O—$R^{18}$, wherein $R^{13}$, $R^{14}$, $R^{15}$, $R^{16}$, $R^{17}$, and $R^{18}$ are independently methyl or ethyl; and w', x', y', and z' are independently an integer from 1 to 10. In some embodiments, w', x', y', and z' are independently 1, 2, or 3. In some embodiments, w', x', y', and z' are independently 4, 5, or 6. In some such embodiments, $R^2$ is —$CH_2$—$CH_2$—O—$CH_3$. In some such embodiments, $R^2$ is —$CH_2$—$CH_2$—O—$CH_2$—$CH_2$—O—$CH_3$. In some such embodiments, In some such embodiments, $R^2$ is —$CH_2$—$CH_2$(—O—$CH_2$—$CH_2$)$_{1-10}$—O—$CH_3$. In some such embodiments, $R^2$ is —$CH_2$—$CH_2$(—O—$CH_2$—$CH_2$)$_2$—O—$CH_3$. In some such embodiments, $R^2$ is —$CH_2$—$CH_2$(—O—$CH_2$—$CH_2$)$_3$—O—$CH_3$. In some such embodiments, $R^2$ is —$CH_2$—$CH_2$(—O—$CH_2$—$CH_2$)$_4$—O—$CH_3$. In some such embodiments, $R^2$ is —$CH_2$—$CH_2$(—O—$CH_2$—$CH_2$)$_5$—O—$CH_3$. In some such embodiments, $R^2$ is —$CH_2$—$CH_2$(—O—$CH_2$—$CH_2$)$_6$—O—$CH_3$. In some such embodiments, $R^2$ is —$CH_2$—$CH_2$(—O—$CH_2$—$CH_2$)$_7$—O—$CH_3$. In some such embodiments, $R^2$ is —$CH_2$—$CH_2$(—O—$CH_2$—$CH_2$)$_8$—O—$CH_3$.

In some embodiments of any of the aforementioned embodiments, $R^2$ is $C_{3-12}$ cycloalkyl, which is optionally substituted one or more times by substituents selected independently from R^x. In some such embodiments, $R^2$ is cyclopentyl. In some such embodiments, $R^2$ is cyclohexyl.

In some embodiments of any of the aforementioned embodiments, $R^1$ and $R^2$ are the same. In some other embodiments of any of the aforementioned embodiments, $R^1$ and $R^2$ are not the same.

In addition to the compounds of formula (I), other compounds may also be suitable for use in passive heating and cooling applications. In some embodiments, such compounds include various hydrocarbons, such as olefins and paraffins. In some other embodiments, such compounds include long-chain diols such as compounds of formula (II):

$$OH\text{---}X^2\text{---}OH \quad (II)$$

wherein $X^2$ is $C_{11\text{-}24}$ alkylene. In some embodiments, $X^2$ is —(CH$_2$)$_{12}$—, —(CH$_2$)$_{14}$—, —(CH$_2$)$_{16}$—, —(CH$_2$)$_{18}$—, —(CH$_2$)$_{20}$—, or —(CH$_2$)$_{22}$—. In some embodiments, $X^2$ is —(CH$_2$)$_{18}$—.

The compounds disclosed above are not limited to any particular use or application. In some embodiments, they can be suitable for use as plasticizers, e.g., for polymer resins. They can be suitable for other uses as well.

Compositions for Passive Heating and Cooling

In further aspects, the disclosure provides passive heating and cooling compositions, which include one or more compounds of any of the aforementioned embodiments (i.e., phase-change compounds).

In some further aspects, the disclosure also provides passive heating and cooling compositions that comprise one or more phase-change compounds selected from the group consisting of: 9-octadecene, octadecanes, pentadecanes, tridecanes, methyl tridecanoate, and methyl pentadecanoate. In some embodiments, the phase-change compound in the composition is 9-octadecene. In some embodiments, the phase-change compound in the composition is methyl tridecanoate. In some embodiments, the phase-change compound in the composition is methyl penadecanoate. In some embodiments, the phase-change compounds in the composition are octadecanes, such as n-octadecane. In some embodiments, the phase-change compounds in the composition are pentadecanes, such as n-pentadecane. In some embodiments, the phase-change compounds in the composition are tridecanes, such as n-tridecane.

These compositions can include one or more of the compounds disclosed herein in any suitable amount. In some embodiments, the composition includes the phase-change compounds, wherein the phase change compounds make up at least 50% by weight, or at least 60% by weight, or at least 70% by weight, or at least 80% by weight of the composition, based on the total weight of the composition. In some embodiments, the composition is made up almost entirely of the phase-change compounds. For example, in some embodiments, the phase change compounds make up at least 90% by weight, or at least 95% by weight, or at least 97% by weight, or at least 99% by weight of the composition, based on the total weight of the composition. In some embodiments, the composition consists essentially of the phase-change compounds. In some embodiments, the composition consists of the phase-change compounds. In any of the aforementioned embodiments, the composition can include one phase-change compound, or, in some other embodiments, can include two or more phase-change compounds.

The compositions can be packaged in any suitable form. For example, in some embodiments, the composition is dispersed or mixed into another medium, such as a polymer, a ceramic material, concrete, etc. In some embodiments, the composition is physically applied or coated onto the surface of a material, such as on the surface of a fiber. For example, in some embodiments, the composition is applied to the surface of a fiber, and is then held substantially in place by the weaving of multiple fibers together, e.g., such that the composition is physically held between multiple fibers. In some other embodiments, however, the composition is encapsulated or contained in another material, such as in a polymeric or waxy encapsulant. In some embodiments, such encapsulants are mixed or dispersed into another medium, such as a polymer, ceramic, concrete, etc. In some other embodiments, however, the composition is contained within a physical structure, such as a physical compartment that is disposed adjacent to (e.g., partially surrounding) another structure, such as a heating device, a cooling device, an electronic or microelectronic structure, a battery cell, an insulated cavity, etc.

Items Incorporating Passive Heating and Cooling Compounds or Compositions

In further aspects, the disclosure provides various items (e.g., structures, apparatuses, materials, etc.) that include one or more phase-change compounds of any of the aforementioned embodiments or one or more compositions of any of the aforementioned embodiments that include phase-change compounds. In some embodiments, the structures, apparatuses, or materials include the following: polymer composites (such as a polymer composite comprising metal wires, metal particles, glass fibers, glass particles, and the like); wax composites (such as a wax composite comprising metal wires, metal particles, glass fibers, glass particles, and the like); insulation materials surrounding parts of a heating apparatus (such as furnaces, ovens, boilers, air ducts, pipes, and the like); insulated storage units; food or drink containers; building materials; medical equipment (such as containers for blood, other biological fluids, and biological tissue, operating tables, and the like); medical packaging, such as hot-cold therapies; textile fibers; clothing articles, jackets, coats, boots, shoes, hats, gloves, scarves, and the like; waste heat recovery apparatuses; water heating and cooling apparatuses; heat pump systems; passive storage structures in bioclimatic buildings; apparatuses for reducing exothermic temperature peaks in chemical reactors or reaction vessels; solar power plants; space suits; spacecraft; vehicle compartment insulation systems; electronic device insulation systems; battery cell insulation or safety systems; computer cooling systems; turbine inlet cooling systems; thermal energy storage systems; and telecommunications shelters.

Use of Passive Heating and Cooling Compounds, Compositions, or Structures

In a further aspects, the disclosure provides methods of storing or releasing thermal energy, the methods comprising: using one or more phase-change compounds of any of the aforementioned embodiments or one or more phase-change compositions of any of the aforementioned embodiments, or one or more of the phase-change structures of any of the aforementioned embodiments.

In some embodiments, the methods are methods for storing thermal energy. In some such embodiments, the using includes: providing one or more phase-change compounds of any of the aforementioned embodiments (e.g., as part of a composition of any of the aforementioned embodiments), wherein at least a portion of the phase-change compounds in the composition are in a solid state; and exposing the composition to a thermal environment having a temperature above the melting point of at least one of the phase-change compounds in the composition (i.e., where said at least one compound was at least partly in a solid state).

In some embodiments, the methods are methods for releasing thermal energy. In some such embodiments, the using includes: providing one or more phase-change compounds of any of the aforementioned embodiments (e.g., as part of a composition of any of the aforementioned embodiments), wherein at least a portion of the phase-change compounds in the composition are in a liquid state; and exposing the composition to a thermal environment having a temperature below the melting point of at least one of the phase-change compounds in the composition (i.e., where said at least one compound was at least partly in a liquid state).

The using can include any suitable manner of using the aforementioned phase-change compounds, compositions, or structures. Such using includes, but is not limited to, incorporating the one or more phase-change compounds (e.g., as part of a phase-change composition or a phase-change structure) into one of more of the following: a polymer composite (such as a polymer composite comprising metal wires, metal particles, glass fibers, or glass particles); a wax composite (such as a wax composite comprising metal wires, metal particles, glass fibers, or glass particles); insulation material surrounding parts of an heating apparatus (such as furnaces, ovens, boilers, air ducts, pipes, and the like); insulated storage units; food or drink containers; building materials; medical equipment (such as containers for blood, other biological fluids, and biological tissue, and operating tables); medical packaging, such as hot-cold therapies); textile fibers; clothing articles, jackets, coats, boots, shoes, hats, gloves, scarves, and the like; waste heat recovery apparatuses; water heating and cooling apparatuses; heat pump systems; passive storage structures in bioclimatic buildings; apparatuses for reducing exothermic temperature peaks in chemical reactors or reaction vessels; solar power plants; space suits; spacecraft; vehicle compartment insulation systems; electronic device insulation systems; battery cell insulation and/or safety systems; computer cooling systems; turbine inlet cooling systems; thermal energy storage systems; and telecommunications shelters.

Methods of Making Diesters

The diacids and diesters disclosed above can be made by conventional means. For example, in some embodiments, the diesters are made by reacting a dibasic acid with an alcohol or a mixture of alcohols to provide the dibasic ester by condensation. In some instances, diesters can also be made by transesterification, where a dibasic ester, such as a dimethyl dibasic ester is reacted with a longer-chain alcohol or mixture of longer-chain alcohols to provide the dibasic ester.

Derivation from Renewable Sources

The compounds employed in any of the aspects or embodiments disclosed herein can, in certain embodiments, be derived from renewable sources, such as from various natural oils or their derivatives. Any suitable methods can be used to make these compounds from such renewable sources. Suitable methods include, but are not limited to, fermentation, conversion by bioorganisms, and conversion by metathesis.

Olefin metathesis provides one possible means to convert certain natural oil feedstocks into olefins and esters that can be used in a variety of applications, or that can be further modified chemically and used in a variety of applications. In some embodiments, a composition (or components of a composition) may be formed from a renewable feedstock, such as a renewable feedstock formed through metathesis reactions of natural oils and/or their fatty acid or fatty ester derivatives. When compounds containing a carbon-carbon double bond undergo metathesis reactions in the presence of a metathesis catalyst, some or all of the original carbon-carbon double bonds are broken, and new carbon-carbon double bonds are formed. The products of such metathesis reactions include carbon-carbon double bonds in different locations, which can provide unsaturated organic compounds having useful chemical properties.

A wide range of natural oils, or derivatives thereof, can be used in such metathesis reactions. Examples of suitable natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

The natural oil may include canola or soybean oil, such as refined, bleached and deodorized soybean oil (i.e., RBD soybean oil). Soybean oil typically includes about 95 percent by weight (wt %) or greater (e.g., 99 wt % or greater) triglycerides of fatty acids. Major fatty acids in the polyol esters of soybean oil include but are not limited to saturated fatty acids such as palmitic acid (hexadecanoic acid) and stearic acid (octadecanoic acid), and unsaturated fatty acids such as oleic acid (9-octadecenoic acid), linoleic acid (9,12-octadecadienoic acid), and linolenic acid (9,12,15-octadecatrienoic acid).

Metathesized natural oils can also be used. Examples of metathesized natural oils include but are not limited to a metathesized vegetable oil, a metathesized algal oil, a metathesized animal fat, a metathesized tall oil, a metathesized derivatives of these oils, or mixtures thereof. For example, a metathesized vegetable oil may include metathesized canola oil, metathesized rapeseed oil, metathesized coconut oil, metathesized corn oil, metathesized cottonseed oil, metathesized olive oil, metathesized palm oil, metathesized peanut oil, metathesized safflower oil, metathesized sesame oil, metathesized soybean oil, metathesized sunflower oil, metathesized linseed oil, metathesized palm kernel oil, metathesized tung oil, metathesized jatropha oil, metathesized mustard oil, metathesized camelina oil, metathesized pennycress oil, metathesized castor oil, metathesized derivatives of these oils, or mixtures thereof. In another example, the metathesized natural oil may include a metathesized animal fat, such as metathesized lard, metathesized tallow, metathesized poultry fat, metathesized fish oil, metathesized derivatives of these oils, or mixtures thereof.

Such natural oils, or derivatives thereof, can contain esters, such as triglycerides, of various unsaturated fatty acids. The identity and concentration of such fatty acids varies depending on the oil source, and, in some cases, on the variety. In some embodiments, the natural oil comprises one or more esters of oleic acid, linoleic acid, linolenic acid, or any combination thereof. When such fatty acid esters are metathesized, new compounds are formed. For example, in embodiments where the metathesis uses certain short-chain olefins, e.g., ethylene, propylene, or 1-butene, and where the natural oil includes esters of oleic acid, an amount of 1-decene and 1-decenoid acid (or an ester thereof), among other products, are formed. Following transesterification, for example, with an alkyl alcohol, an amount of 9-denenoic acid alkyl ester is formed. In some such embodiments, a separation step may occur between the metathesis and the transesterification, where the alkenes are separated from the esters. In some other embodiments, transesterification can occur before metathesis, and the metathesis is performed on the transesterified product.

In some embodiments, the natural oil can be subjected to various pre-treatment processes, which can facilitate their utility for use in certain metathesis reactions. Useful pre-treatment methods are described in United States Patent Application Publication Nos. 2011/0113679, 2014/0275595, and 2014/0275681, all three of which are hereby incorporated by reference as though fully set forth herein.

In some embodiments, after any optional pre-treatment of the natural oil feedstock, the natural oil feedstock is reacted in the presence of a metathesis catalyst in a metathesis reactor. In some other embodiments, an unsaturated ester (e.g., an unsaturated glyceride, such as an unsaturated triglyceride) is reacted in the presence of a metathesis catalyst in a metathesis reactor. These unsaturated esters may be a component of a natural oil feedstock, or may be derived from other sources, e.g., from esters generated in earlier-performed metathesis reactions. In certain embodiments, in the presence of a metathesis catalyst, the natural oil or unsaturated ester can undergo a self-metathesis reaction with itself. In other embodiments, the natural oil or unsaturated ester undergoes a cross-metathesis reaction with the low-molecular-weight olefin or mid-weight olefin. The self-metathesis and/or cross-metathesis reactions form a metathesized product wherein the metathesized product comprises olefins and esters.

In some embodiments, the low-molecular-weight olefin (or short-chain olefin) is in the $C_{2-6}$ range. As a non-limiting example, in one embodiment, the low-molecular-weight olefin may comprise at least one of: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. In some embodiments, the short-chain olefin is 1-butene. In some instances, a higher-molecular-weight olefin can also be used.

In some embodiments, the metathesis comprises reacting a natural oil feedstock (or another unsaturated ester) in the presence of a metathesis catalyst. In some such embodiments, the metathesis comprises reacting one or more unsaturated glycerides (e.g., unsaturated triglycerides) in the natural oil feedstock in the presence of a metathesis catalyst. In some embodiments, the unsaturated glyceride comprises one or more esters of oleic acid, linoleic acid, linolenic acid, or combinations thereof. In some other embodiments, the unsaturated glyceride is the product of the partial hydrogenation and/or the metathesis of another unsaturated glyceride (as described above). In some such embodiments, the metathesis is a cross-metathesis of any of the aforementioned unsaturated triglyceride species with another olefin, e.g., an alkene. In some such embodiments, the alkene used in the cross-metathesis is a lower alkene, such as ethylene, propylene, 1-butene, 2-butene, etc. In some embodiments, the alkene is ethylene. In some other embodiments, the alkene is propylene. In some further embodiments, the alkene is 1-butene. And in some even further embodiments, the alkene is 2-butene.

Metathesis reactions can provide a variety of useful products, when employed in the methods disclosed herein. For example, the unsaturated esters may be derived from a natural oil feedstock, in addition to other valuable compositions. Moreover, in some embodiments, a number of valuable compositions can be targeted through the self-metathesis reaction of a natural oil feedstock, or the cross-metathesis reaction of the natural oil feedstock with a low-molecular-weight olefin or mid-weight olefin, in the presence of a metathesis catalyst. Such valuable compositions can include fuel compositions, detergents, surfactants, and other specialty chemicals. Additionally, transesterified products (i.e., the products formed from transesterifying an ester in the presence of an alcohol) may also be targeted, non-limiting examples of which include: fatty acid methyl esters ("FAMEs"); biodiesel; 9-decenoic acid ("9DA") esters, 9-undecenoic acid ("9UDA") esters, and/or 9-dodecenoic acid ("9DDA") esters; 9DA, 9UDA, and/or 9DDA; alkali metal salts and alkaline earth metal salts of 9DA, 9UDA, and/or 9DDA; dimers of the transesterified products; and mixtures thereof.

Further, in some embodiments, multiple metathesis reactions can also be employed. In some embodiments, the multiple metathesis reactions occur sequentially in the same reactor. For example, a glyceride containing linoleic acid can be metathesized with a terminal lower alkene (e.g., ethylene, propylene, 1-butene, and the like) to form 1,4-decadiene, which can be metathesized a second time with a terminal lower alkene to form 1,4-pentadiene. In other embodiments, however, the multiple metathesis reactions are not sequential, such that at least one other step (e.g., transesterification, hydrogenation, etc.) can be performed between the first metathesis step and the following metathesis step. These multiple metathesis procedures can be used to obtain products that may not be readily obtainable from a single metathesis reaction using available starting materials. For example, in some embodiments, multiple metathesis can involve self-metathesis followed by cross-metathesis to obtain metathesis dimers, trimmers, and the like. In some other embodiments, multiple metathesis can be used to obtain olefin and/or ester components that have chain lengths that may not be achievable from a single metathesis reaction with a natural oil triglyceride and typical lower alkenes (e.g., ethylene, propylene, 1-butene, 2-butene, and the like). Such multiple metathesis can be useful in an industrial-scale reactor, where it may be easier to perform multiple metathesis than to modify the reactor to use a different alkene.

For example, multiple metathesis can be employed to make the dibasic acid compounds used to make the diesters disclosed herein. In some embodiments, alkyl (e.g., methyl) esters of 9-decenoic acid, 9-undecenoic acid, 9-dodecenoic acid, or any combination thereof, can be reacted in a self-metathesis reaction or a cross-metathesis to generate various unsaturated dibasic alkyl esters, such as dimethyl 9-octadecendioate. Such compounds can then be converted to dibasic acids by hydrolysis or via saponification followed by acidification. If a saturated dibasic acid is desired, the compound can be hydrogenated, either before conversion to the acid or after. Dibasic acids of other chain lengths can be made by analogous means.

The conditions for such metathesis reactions, and the reactor design, and suitable catalysts are as described below with reference to the metathesis of the olefin esters. That discussion is incorporated by reference as though fully set forth herein.

Olefin Metathesis

In some embodiments, one or more of the unsaturated monomers can be made by metathesizing a natural oil or natural oil derivative. The terms "metathesis" or "metathesizing" can refer to a variety of different reactions, including, but not limited to, cross-metathesis, self-metathesis, ring-opening metathesis, ring-opening metathesis polymerizations ("ROMP"), ring-closing metathesis ("RCM"), and acyclic diene metathesis ("ADMET"). Any suitable metathesis reaction can be used, depending on the desired product or product mixture.

In some embodiments, after any optional pre-treatment of the natural oil feedstock, the natural oil feedstock is reacted in the presence of a metathesis catalyst in a metathesis reactor. In some other embodiments, an unsaturated ester (e.g., an unsaturated glyceride, such as an unsaturated triglyceride) is reacted in the presence of a metathesis catalyst in a metathesis reactor. These unsaturated esters may be a component of a natural oil feedstock, or may be derived from other sources, e.g., from esters generated in earlier-performed metathesis reactions. In certain embodiments, in the presence of a metathesis catalyst, the natural oil or unsaturated ester can undergo a self-metathesis reaction with itself. In other embodiments, the natural oil or unsaturated ester undergoes a cross-metathesis reaction with the low-molecular-weight olefin or mid-weight olefin. The self-metathesis and/or cross-metathesis reactions form a metathesized product wherein the metathesized product comprises olefins and esters.

In some embodiments, the low-molecular-weight olefin is in the $C_{2-6}$ range. As a non-limiting example, in one embodiment, the low-molecular-weight olefin may comprise at least one of: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. In some instances, a higher-molecular-weight olefin can also be used.

In some embodiments, the metathesis comprises reacting a natural oil feedstock (or another unsaturated ester) in the presence of a metathesis catalyst. In some such embodiments, the metathesis comprises reacting one or more unsaturated glycerides (e.g., unsaturated triglycerides) in the natural oil feedstock in the presence of a metathesis catalyst. In some embodiments, the unsaturated glyceride comprises one or more esters of oleic acid, linoleic acid, linoleic acid, or combinations thereof. In some other embodiments, the unsaturated glyceride is the product of the partial hydrogenation and/or the metathesis of another unsaturated glyceride (as described above). In some such embodiments, the metathesis is a cross-metathesis of any of the aforementioned unsaturated triglyceride species with another olefin, e.g., an alkene. In some such embodiments, the alkene used in the cross-metathesis is a lower alkene, such as ethylene, propylene, 1-butene, 2-butene, etc. In some embodiments, the alkene is ethylene. In some other embodiments, the alkene is propylene. In some further embodiments, the alkene is 1-butene. And in some even further embodiments, the alkene is 2-butene.

Metathesis reactions can provide a variety of useful products, when employed in the methods disclosed herein. For example, terminal olefins and internal olefins may be derived from a natural oil feedstock, in addition to other valuable compositions. Moreover, in some embodiments, a number of valuable compositions can be targeted through the self-metathesis reaction of a natural oil feedstock, or the cross-metathesis reaction of the natural oil feedstock with a low-molecular-weight olefin or mid-weight olefin, in the presence of a metathesis catalyst. Such valuable compositions can include fuel compositions, detergents, surfactants, and other specialty chemicals. Additionally, transesterified products (i.e., the products formed from transesterifying an ester in the presence of an alcohol) may also be targeted, non-limiting examples of which include: fatty acid methyl esters ("FAMEs"); biodiesel; 9-decenoic acid ("9DA") esters, 9-undecenoic acid ("9UDA") esters, and/or 9-dodecenoic acid ("9DDA") esters; 9DA, 9UDA, and/or 9DDA; alkali metal salts and alkaline earth metal salts of 9DA, 9UDA, and/or 9DDA; dimers of the transesterified products; and mixtures thereof.

Further, in some embodiments, the methods disclosed herein can employ multiple metathesis reactions. In some embodiments, the multiple metathesis reactions occur sequentially in the same reactor. For example, a glyceride containing linoleic acid can be metathesized with a terminal lower alkene (e.g., ethylene, propylene, 1-butene, and the like) to form 1,4-decadiene, which can be metathesized a second time with a terminal lower alkene to form 1,4-pentadiene. In other embodiments, however, the multiple metathesis reactions are not sequential, such that at least one other step (e.g., transesterification, hydrogenation, etc.) can be performed between the first metathesis step and the following metathesis step. These multiple metathesis procedures can be used to obtain products that may not be readily obtainable from a single metathesis reaction using available starting materials. For example, in some embodiments, multiple metathesis can involve self-metathesis followed by cross-metathesis to obtain metathesis dimers, trimmers, and the like. In some other embodiments, multiple metathesis can be used to obtain olefin and/or ester components that have chain lengths that may not be achievable from a single metathesis reaction with a natural oil triglyceride and typical lower alkenes (e.g., ethylene, propylene, 1-butene, 2-butene, and the like). Such multiple metathesis can be useful in an industrial-scale reactor, where it may be easier to perform multiple metathesis than to modify the reactor to use a different alkene.

The metathesis process can be conducted under any conditions adequate to produce the desired metathesis products. For example, stoichiometry, atmosphere, solvent, temperature, and pressure can be selected by one skilled in the art to produce a desired product and to minimize undesirable byproducts. In some embodiments, the metathesis process may be conducted under an inert atmosphere. Similarly, in embodiments where a reagent is supplied as a gas, an inert gaseous diluent can be used in the gas stream. In such embodiments, the inert atmosphere or inert gaseous diluent typically is an inert gas, meaning that the gas does not interact with the metathesis catalyst to impede catalysis to a substantial degree. For example, non-limiting examples of inert gases include helium, neon, argon, and nitrogen, used individually or in with each other and other inert gases.

The rector design for the metathesis reaction can vary depending on a variety of factors, including, but not limited to, the scale of the reaction, the reaction conditions (heat, pressure, etc.), the identity of the catalyst, the identity of the materials being reacted in the reactor, and the nature of the feedstock being employed. Suitable reactors can be designed by those of skill in the art, depending on the relevant factors, and incorporated into a refining process such, such as those disclosed herein.

The metathesis reactions disclosed herein generally occur in the presence of one or more metathesis catalysts. Such methods can employ any suitable metathesis catalyst. The metathesis catalyst in this reaction may include any catalyst or catalyst system that catalyzes a metathesis reaction. Any known metathesis catalyst may be used, alone or in combination with one or more additional catalysts. Examples of metathesis catalysts and process conditions are described in US 2011/0160472, incorporated by reference herein in its entirety, except that in the event of any inconsistent disclosure or definition from the present specification, the disclosure or definition herein shall be deemed to prevail. A number of the metathesis catalysts described in US 2011/0160472 are presently available from Materia, Inc. (Pasadena, Calif.).

In some embodiments, the metathesis catalyst includes a Grubbs-type olefin metathesis catalyst and/or an entity derived therefrom. In some embodiments, the metathesis catalyst includes a first-generation Grubbs-type olefin metathesis catalyst and/or an entity derived therefrom. In some embodiments, the metathesis catalyst includes a second-generation Grubbs-type olefin metathesis catalyst and/or an entity derived therefrom. In some embodiments, the metathesis catalyst includes a first-generation Hoveyda-Grubbs-type olefin metathesis catalyst and/or an entity derived therefrom. In some embodiments, the metathesis catalyst includes a second-generation Hoveyda-Grubbs-type olefin metathesis catalyst and/or an entity derived therefrom. In some embodiments, the metathesis catalyst includes one or a plurality of the ruthenium carbene metathesis catalysts sold by Materia, Inc. of Pasadena, Calif. and/or one or more entities derived from such catalysts. Representative metathesis catalysts from Materia, Inc. for use in accordance with the present teachings include but are not limited to those sold under the following product numbers as well as combinations thereof: product no. C823 (CAS no. 172222-30-9), product no. C848 (CAS no. 246047-72-3), product no. C601 (CAS no. 203714-71-0), product no. C627 (CAS no. 301224-40-8), product no. C571 (CAS no. 927429-61-6), product no. C598 (CAS no. 802912-44-3), product no. C793 (CAS no. 927429-60-5), product no. C801 (CAS no. 194659-03-9), product no. C827 (CAS no. 253688-91-4), product no. C884 (CAS no. 900169-53-1), product no. C833 (CAS no. 1020085-61-3), product no. C859 (CAS no. 832146-68-6), product no. C711 (CAS no. 635679-24-2), product no. C933 (CAS no. 373640-75-6).

In some embodiments, the metathesis catalyst includes a molybdenum and/or tungsten carbene complex and/or an entity derived from such a complex. In some embodiments, the metathesis catalyst includes a Schrock-type olefin metathesis catalyst and/or an entity derived therefrom. In some embodiments, the metathesis catalyst includes a high-oxidation-state alkylidene complex of molybdenum and/or an entity derived therefrom. In some embodiments, the metathesis catalyst includes a high-oxidation-state alkylidene complex of tungsten and/or an entity derived therefrom. In some embodiments, the metathesis catalyst includes molybdenum (VI). In some embodiments, the metathesis catalyst includes tungsten (VI). In some embodiments, the metathesis catalyst includes a molybdenum- and/or a tungsten-containing alkylidene complex of a type described in one or more of (a) Angew. Chem. Int. Ed. Engl., 2003, 42, 4592-4633; (b) Chem. Rev., 2002, 102, 145-179; and/or (c) Chem. Rev., 2009, 109, 3211-3226, each of which is incorporated by reference herein in its entirety, except that in the event of any inconsistent disclosure or definition from the present specification, the disclosure or definition herein shall be deemed to prevail.

In certain embodiments, the metathesis catalyst is dissolved in a solvent prior to conducting the metathesis reaction. In certain such embodiments, the solvent chosen may be selected to be substantially inert with respect to the metathesis catalyst. For example, substantially inert solvents include, without limitation: aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc. In some embodiments, the solvent comprises toluene.

In other embodiments, the metathesis catalyst is not dissolved in a solvent prior to conducting the metathesis reaction. The catalyst, instead, for example, can be slurried with the natural oil or unsaturated ester, where the natural oil or unsaturated ester is in a liquid state. Under these conditions, it is possible to eliminate the solvent (e.g., toluene) from the process and eliminate downstream olefin losses when separating the solvent. In other embodiments, the metathesis catalyst may be added in solid state form (and not slurried) to the natural oil or unsaturated ester (e.g., as an auger feed).

The metathesis reaction temperature may, in some instances, be a rate-controlling variable where the temperature is selected to provide a desired product at an acceptable rate. In certain embodiments, the metathesis reaction temperature is greater than −40° C., or greater than −20° C., or greater than 0° C., or greater than 10° C. In certain embodiments, the metathesis reaction temperature is less than 200° C., or less than 150° C., or less than 120° C. In some embodiments, the metathesis reaction temperature is between 0° C. and 150° C., or is between 10° C. and 120° C.

The metathesis reaction can be run under any desired pressure. In some instances, it may be desirable to maintain a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than 0.1 atm (10 kPa), or greater than 0.3 atm (30 kPa), or greater than 1 atm (100 kPa). In some embodiments, the reaction pressure is no more than about 70 atm (7000 kPa), or no more than about 30 atm (3000 kPa). In some embodiments, the pressure for the metathesis reaction ranges from about 1 atm (100 kPa) to about 30 atm (3000 kPa).

EXAMPLES

Example 1—Bis(4-methylbutyl)Octadecanedioate 1,18-Octadecanedioic acid (ODDA) was added to a 100-mL three-necked round-bottom flask. A Dean-Stark condenser was attached, followed by the addition of toluene to the ODDA and to the trap. 4-Methylbutyl (isoamyl) alcohol was added to the ODDA mixture. The flask was immediately purged with nitrogen gas and p-toluenesulfonic acid was added. The reaction mixture was heated and the reaction proceeded for several hours. Heat was then removed and the reaction mixture was allowed to cool, at which point aqueous $NaHCO_3$ was added to achieve a neutral pH. After vigorous stirring, the organic layer was separated and dried over $Na_2SO_4$. The dried product was then subjected to a vacuum treatment to remove any residual solvent.

The melting point and enthalpy of fusion were determined using differential scanning calorimetry (DSC). The bis(3-methylbutyl) octadecanedioate was determined to have a melting temperature ($T_m$) of 38.5° C. and an enthalpy of fusion of 148 J/g, indicating its suitability as a phase-change material for applications where there is a desire to maintain a temperature near human body temperature.

Example 2—Bis(3,5,5-trimethylhexyl) Octadecanedioate

Bis(3,5,5-trimethylhexyl) octadecanedioate was made from octadecanedioic acid (ODDA) and 3,5,5-trimethylhexyl alcohol by means analogous to those used for Example 1.

The melting point and enthalpy of fusion were determined using differential scanning calorimetry (DSC). The bis(3,5,5-trimethylhexyl) octadecanedioate was determined to have a melting temperature ($T_m$) of 20.5° C. and an enthalpy of fusion of 119 J/g, indicating its suitability as a phase-change material for applications where there is a desire to maintain a temperature near room temperature.

Example 3—Bis(3,5,5-trimethylhexyl) Octadecanedioate

Bis(triethylene glycol monomethyl ether) octadecanedioate was made from octadecanedioic acid (ODDA) and triethylene glycol monomethyl ether by means analogous to those used for Example 1.

The melting point and enthalpy of fusion were determined using differential scanning calorimetry (DSC). The bis(triethylene glycol monomethyl ether) octadecanedioate was determined to have a melting temperature ($T_m$) of 15.4° C. and an enthalpy of fusion of 148 J/g, indicating its suitability as a phase-change material for applications where there is a desire to maintain a temperature somewhat below room temperature, such as for wine storage.

Example 4—Dimethyl Octadecanedioate

Dimethyl 1,18-octadecanedioate was obtained from Elevance Renewable Sciences, Inc. (Woodridge, Ill., USA) in substantially pure form.

The melting point and enthalpy of fusion were determined using differential scanning calorimetry (DSC). The dimethyl 1,18-octadecanedioate was determined to have a melting temperature ($T_m$) of 57.1° C. and an enthalpy of fusion of 209 J/g, indicating its suitability as a phase-change material for applications where there is a desire to maintain a temperature somewhat above room temperature, such as for a food serving line.

Example 5—Octadecanedioic Acid 1,18-Octadecanedioic acid (ODDA) was obtained from Elevance Renewable Sciences, Inc. (Woodridge, Ill., USA) in substantially pure form.

The melting point and enthalpy of fusion were determined using differential scanning calorimetry (DSC). The 1,18-octadecanedioic acid was determined to have a melting temperature ($T_m$) of 130.2° C. and an enthalpy of fusion of 219 J/g, indicating its suitability as a phase-change material for applications where there is a desire to maintain an elevated temperature.

Example 6—Octadecane Diol 1,18-Octadecane diol was obtained by hydrogenating the ODDA from Elevance Renewable Sciences, Inc. (Woodridge, Ill., USA).

The melting point and enthalpy of fusion were determined using differential scanning calorimetry (DSC). The 1,18-octadecane diol was determined to have a melting temperatures ($T_m$) of 92.2° C. and 97.5° C., and an enthalpy of fusion of 103 J/g and 85 J/g, respectively, indicating its suitability as a phase-change material for applications where there is a desire to maintain a temperature near the boiling temperature of water.

Example 7—Dimethyl cis/trans-1,18-Octadec-9-enedioate

Dimethyl cis/trans-1,18-octadec-9-enedioate was obtained from Elevance Renewable Sciences, Inc. (Woodridge, Ill., USA) in substantially pure form.

The melting point and enthalpy of fusion were determined using differential scanning calorimetry (DSC). The dimethyl cis/trans-1,18-octadec-9-enedioate was determined to have a melting temperature ($T_m$) of 26.8° C. and an enthalpy of fusion of 259 J/g, indicating its suitability as a phase-change material for applications where there is a desire to maintain a temperature near room temperature.

What is claimed is:

1. A method of storing or releasing thermal energy, the method comprising:
using a compound of formula (I):

wherein:
$X^1$ is —$(CH_2)_{16}$—, —$(CH_2)_{18}$—, —$(CH_2)_{20}$—, or —$(CH_2)_{22}$—;
$R^1$ is $C_{1-12}$ oxyalkyl, which is optionally substituted one or more times by substituents selected independently from the group consisting of —OH and $C_{1-6}$ oxyalkyl;
$R^2$ is a $C_{1-12}$ alkyl, $C_{2-12}$ alkenyl, $C_{1-12}$ oxyalkyl, $C_{3-12}$ cycloalkyl, or $C_{2-12}$ heterocyclyl, each of which is optionally substituted one or more times by substituents selected independently from $R^x$, or $R^2$ is a hydrogen atom;
$R^x$ is a halogen atom, —OH, —$NH_2$, $C_{1-6}$ alkyl, $C_{1-6}$ heteroalkyl, or $C_{2-6}$ alkenyl.

2. The method of claim 1, wherein $X^1$ is —$(CH_2)_{16}$—.
3. The method of claim 1, wherein $R^2$ is a hydrogen atom.
4. The method of claim 1, wherein $R^2$ is $C_{1-12}$ alkyl, which is optionally substituted one or more times by substituents selected independently from $R^x$.

5. The method of claim 1, wherein $R^2$ is $C_{1-12}$ oxyalkyl, which is optionally substituted one or more times by substituents selected independently from the group consisting of —OH and $C_{1-6}$ oxyalkyl.

6. The method of claim 1, wherein $R^2$ is $C_{3-12}$ cycloalkyl, which is optionally substituted one or more times by substituents selected independently from $R^x$.

7. The method of claim 1, wherein the method comprises a method for storing thermal energy.

8. The method of claim 7, wherein the method is a method for storing thermal energy, and wherein the using comprises:
    providing a composition comprising the compound of formula (I), wherein at least a portion of the compound in the composition is in a solid state; and
    exposing the composition to a thermal environment having a temperature above the melting point of the compound.

9. The method of claim 8, wherein the composition consists of or consists essentially of the compound of formula (I).

10. The method of claim 1, wherein the method comprises a method for releasing thermal energy.

11. The method of claim 10, wherein the method is a method of releasing thermal energy and the using comprises:
    providing a composition comprising the compound of formula (I), wherein at least a portion of the compound in the composition is in a liquid state; and
    exposing the composition to a thermal environment having a temperature below the melting point of the compound.

12. The method of claim 11, wherein the composition consists of or consists essentially of the compound of formula (I).

* * * * *